United States Patent [19]

Scharf et al.

[11] Patent Number: 4,485,249

[45] Date of Patent: Nov. 27, 1984

[54] 2-ACYLATED DIHYDRO-1,3-DIOXEPINS, PROCESS FOR THE PRODUCTION THEREOF AND USE THEREOF AS PHOTO-INITIATORS

[75] Inventors: Hans-Dieter Scharf, Roetgen; Herbert Fraüenrath, Aachen; Hans-Georg Heine, Krefeld; Hans Rudolph, Krefeld; Karl-Friedrich Neuhaus, Krefeld; Otto Bendszus, Krefeld, all of Fed. Rep. of Germany

[73] Assignee: Ciba-Geigy Corporation, Ardsley, N.Y.

[21] Appl. No.: 511,538

[22] Filed: Jul. 7, 1983

[30] Foreign Application Priority Data

Jul. 16, 1982 [DE] Fed. Rep. of Germany ....... 3226617

[51] Int. Cl.$^3$ ............................................ C07D 321/06
[52] U.S. Cl. ................................. 549/347; 204/159.23
[58] Field of Search .......................................... 549/347

[56] References Cited

U.S. PATENT DOCUMENTS 3,134,788   5/1964   Sterling et al. ..................... 549/347

Primary Examiner—Norma S. Milestone
Attorney, Agent, or Firm—Harry Falber

[57] ABSTRACT

2-Acylated dihydro-1,3-dioxepins proved to be highly reactive photoinitiators having a low tendency towards yellowing.

3 Claims, No Drawings

2-ACYLATED DIHYDRO-1,3-DIOXEPINS, PROCESS FOR THE PRODUCTION THEREOF AND USE THEREOF AS PHOTO-INITIATORS

This invention relates to dihydro-1,3-dioxepins, acylated in the 2-position, to a process for the production thereof by reacting 2-butene-1,4-diol with a benzil or with a benzil monoketal, and to the use of these dihydro-1,3-dioxepins as photo-initiators.

The use as photo-initiators of photosensitive compounds which form radicals on irradiation has long been known (survey: J. Kosar, Light-Sensitive Systems, Wiley N.Y. 1965). One of the photo-initiators which have also been commercially available, is benzil-dimethylketal. The high reactivity thereof is greatly valued, although it has a disadvantage in that coatings produced therewith yellow under the influence of light. Therefore, an object of the present invention is to provide photo-initiators which have a lower tendency towards yellowing and which at least achieve the reactivity of benzil-dimethylketal, but as far as possible surpass this reactivity.

Surprisingly, it has been found that 2-acylated dihydro-1,3-dioxepins corresponding to the following general formulae:

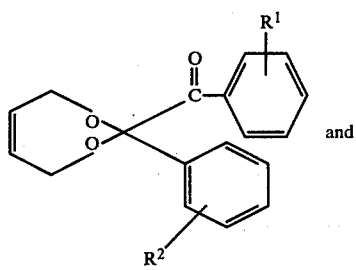

and

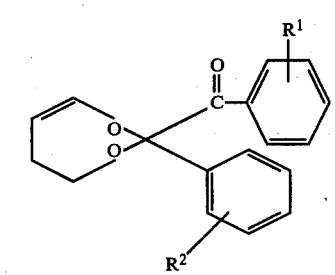

are highly reactive initiators which allow the production of photo-hardened coatings having a substantially reduced yellowing tendency.

The compounds (I) according to the present invention may be produced by the reaction of cis-2-butene-1,4-diol with benzils corresponding to the following general formula:

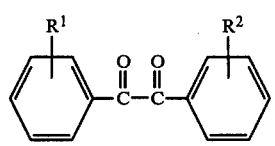

or with benzil monoketals corresponding to the following general formula:

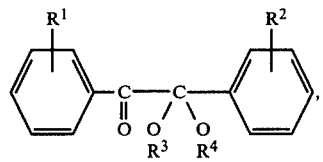

wherein
$R^1$ and $R^2$ independently represent a hydrogen atom, a $C_1-C_4$ alkoxy or alkyl radical, or a halogen atom; and
$R^3$ and $R^4$ independently represent a $C_1-C_4$ alkyl radical.

The reaction is preferably carried out in the presence of an acid catalyst, but particularly in the presence of thionyl chloride and a diluent.

The compounds (II) according to the present invention may be produced by isomerisation of the compounds (I). Strong bases or transition metal hydrides may be used as isomerisation catalysts.

It is known to react aromatic 1,2-diketones with primary monohydric alcohols in the presence of a derivative of sulphurous acid, for example dialkyl sulphite and thionyl chloride, to produce the corresponding monoketals (DE-AS No. 2,337,813). As far as is known, a commercially usable one-stage synthesis of cyclic monoketals of aromatic 1,2-diketones is hitherto unknown. The production process according to the present invention is all the more surprising since, for example, with acid catalysis, benzil even reacts with small quantities of ethylene glycol to produce the bisketal (Rec. Trav. Chim. 57, 133 (1938)). However, it is also surprising that cis-2-butene-1,4-diol is not appreciably dehydrated under the reaction conditions (see Compt. rend. 233. 907 (1946); J. Amer. Chem. Soc. 54 4385 (1932)). It is a surprising feature of ketalisation in the presence of thionyl chloride that no reaction between the thionyl chloride and the 2 butene-1,4-diol is observed (see, for example, J. Org. Chem. 39, 848 (1974); Bull. Inst. Chem. Res., Kyoto Univ. 1971, 49(3), 179-99).

Therefore, the present invention provides compounds corresponding to the following general formula:

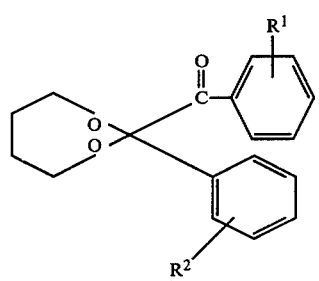

wherein
$R^1$ and $R^2$ independently represent a hydrogen atom, a $C_1-C_4$ alkoxy or alkyl radical, preferably a methyl radical, or a halogen atom, preferably a chlorine atom.

The present invention also provides a process for the production of the compounds (V) by the reaction of cis-2-butene-1,4-diol with a benzil corresponding to the following general formula:

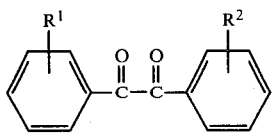

or with a benzil monoketal corresponding to the following general formula:

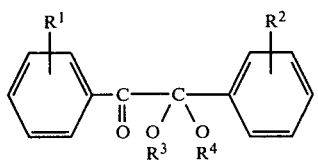

wherein
$R^1$ and $R^2$ are as defined above; and
$R^3$ and $R^4$ independently represent a $C_1$–$C_4$ alkyl radical; and optionally by subsequent isomerisation The present invention further provides the use of the compounds (V) as photo-initiators, preferably in the UV range of from 200 to 500 nm, in particular from 300 to 450 nm.

Preferred 1,2-diketones (III) include benzil, 4,4'-dimethylbenzil, 4,4'-dichlorobenzil, 4-methylbenzil, 3-methoxybenzil and 4-chlorobenzil.

Preferred monoketals (IV) include benzil-dimethylketal, benzil-diethylketal, benzil-dipropylketal, 4,4'-dimethylbenzil-dimethylketal, 4,4'-dichlorobenzil-dimethylketal and 4-chlorobenzil-dimethylketal. Since ethanol and, above all, methanol are particularly easy to remove from the reaction mixture, it is advisable to use the respective dimethyl or diethylketals.

The process according to the present invention may be carried out in a diluent which is optionally simultaneously used as an entrainer for the water produced by the reaction. Preferred diluents include, for example: benzene, toluene, methanol, ethanol, isopropanol, isobutanol and excess cis-2-butene-1,4-diol. If cis-butene-1,4-diol is used as the diluent, it is advisable to carry out the reaction under reduced pressure in order to remove volatile reaction products (water, alcohols) from the reaction mixture.

To carry out the present process, the benzil (III) or monoketal (IV) is combined with cis-2-butene-1,4-diol, optionally with the addition of a diluent and/or a catalyst.

Thionyl chloride and p-toluene sulphonic acid are particularly suitable as catalysts for the present process, starting from benzil (III), and sulphuric acid, p-toluene sulphonic acid, phosphoric acid, hydrogen chloride, boron trifluoride etherate, thionyl chloride and acid ion exchangers are particularly suitable as catalysts starting from the monoketal (IV), (see "Methoden der Organischen Chemie" (Houben-Weyl), volume VI/3, p. 203 ff., in particular p. 207 and 215, Georg Thieme Verlag, Stuttgart 1965). The catalysts are usually used in quantities of form 0.1 to 5%, by weight, based on the starting material (III) or (IV).

While the reactions which are catalysed with thionyl chloride are usually carried out at from −20° to +20° C., the reactions accelerated with other catalysts are generally performed by heating to a temperature of from 40° to 110° C., preferably from 50° to 80° C. The progress of the reaction may be followed by thin layer chromatography. The reaction mixture is usually neutralized and, if a water-soluble diluent is used, this is removed and, if a water-soluble diluent is used, the reaction product is precipitated with water. If the resulting crude product is to be further purified, a distillation or re-crystallisation procedure may be carried out subsequently.

In order to isomerise the 4,7-dihydro-1,3-dioxepins (I) into 4,5-dihydro-1,3-dioxepins (II), the process according to Chem Ber. 113, 1472 (1980), or that according to H. Suzuki et al., Tetrahedron Letters 1980, 4927, may be carried out. Preferred isomerisation catalysts include strong bases, such as potassium-t-butylate, and transition metal hydrides, for example ruthenium hydride.

Examples of compounds corresponding to general formula (V) include the following:
2-benzoyl-2-phenyl-4,7-dihydro-1,3-dioxepin,
2-benzoyl-2-phenyl-4,5-dihydro-1,3-dioxepin,
2-(4-methylbenzoyl)-2-(4-methylphenyl)-4,7-dihydro-1,3-dioxepin and
2-(4-chlorobenzoyl)-2-(4-chlorophenyl)-4,7-dihydro-1,3-dioxepin.

All radically polymerisable compounds or mixtures are included as substances, the polymerisation of which may be initiated by the compounds (V) according to the present invention, i.e., for example olefins, such as ethylene, conjugated dienes, such as butadiene, isoprene and chloroprene; vinyl chloride, vinylidene chloride; aromatic vinyl compounds, such as styrene, divinyl benzene, vinyl esters, in particular vinyl acetate and vinyl propionate; vinyl ethers, such as vinyl propyl ether, vinyl isobutyl ether; acrylic acid and methacrylic acid and derivatives thereof, such as esters, in particular with aliphatic alcohols having from 1 to 5 carbon atoms, nitriles, amides; di(vinyl phenyl)carbonates; diallyl phthalate, diallyl carbonate, diallyl fumarate; di-(allyl phenyl)carbonates; polyol-poly(meth)acrylates; and N,N'-methylene-bis-(meth)acrylamide.

Substances which are more preferably to be polymerised include prepolymers containing (meth)acryloyl groups, for example polyester(meth)acrylate, epoxy(meth)acrylate, urethane(meth)acrylate and unsaturated polyesters which may optionally be diluted with reactive diluents, for example (meth)acrylates or styrene. In the present context, the term "(meth)acrylate" embraces acrylic acid derivatives and methacrylic acid derivatives, as well as mixtures of these components.

Preferred α,β-ethylenically unsaturated polyesters include the conventional polycondensation products of at least one α,β-ethylenically unsaturated dicarboxylic acid usually having 4 or 5 carbon atoms, or ester-forming derivatives thereof, for example anhydrides thereof, optionally in admixture with up to 200 mol %, based on the unsaturated acid components, of at least one aliphatic saturated dicarboxylic acid having from 4 to 10 carbon atoms or a cycloaliphatic or aromatic dicarboxylic acid having from 8 to 10 carbon atoms or ester-forming derivatives thereof with at least one polyhydroxy compound, in particular dihydroxy compound, having from 2 to 8 carbon atoms, i.e. polyesters of the type described by J. Björksten et al. in "Polyesters and their Applications", Reinhold Publishing Corp., New York 1956.

Other systems which may be hardened using the compounds (V) according to the present invention are described in, for example DE-OS Nos. 2,737,406 and 2,841,880.

For use as photoinitiators the compounds V according to the invention can be used in conventional amounts, preferably in amounts of from 1 to 5% by weight, related to polymerizable compounds.

EXAMPLES

A 1. Production of the binders

1. Production of a urethane acrylate 1065.6 g of isophorone diisocyanate, 0.11 g of tin octoate and 0.53 g of 2,5-di-t-butyl hydroquinone were heated to from 50° to 60° C., and 445.4 g of hydroxy ethyl acrylate were added dropwise with stirring while dry air was passed over. After reaching an NCO value of 16.1%, by weight, 3.1 g of tin octoate were added, and while maintaining the temperature, 74.88 g of thiodiglycol and 1080 g of an ethoxylated trimethylolpropane having an OH number of 250 were added. The mixture was mixed with 1120 g of hexane diol-1,6-bisacrylate and stirred at 65° C. until the NCO value fell below 0.1%, by weight (binder 1).

2. Production of an unsaturated polyester resin

A polyester having an acid number of from 15 to 20 was produced from 2157 g of maleic acid anhydride, 451 g of propylene glycol, 1441 g of diethylene glycol, 941.3 g of trimethylolpropane diallyl ether and 428.3 g of diethylene glycol monobutyl ether by melt condensation. The resulting polyester was diluted with styrene to produce a 70%, by weight, solution (binder 2).

A 2. Production of the reactive diluent (I) Production of oxyethylated trimethylolpropane having an oxyethylation degree of 3.75

402 g of trimethylolpropane were mixed with 1 g of sodium methylate and heated to 100° C. in a flask equipped with a gas inlet pipe, a stirrer and a thermometer. 495 g of ethylene oxide were slowly introduced. At the end of the reaction, the flask was evacuated for a short time and then cooled. A colourless product was obtained having an OH number of 550 and a viscosity of 500 cP at 20° Höppler viscosimeter.

The product had the following composition, as determined by gas chromatography:
4%, by weight, of mono-oxethylation product,
14%, by weight, of dioxethylation product,
29%, by weight, of trioxethylation product,
30%, by weight, of tetra-oxethylation product,
16%, by weight, of penta-oxethylation product, and
6%, by weight, of hexa-oxethylation product.

(II) Production of the triacrylate of the oxethylated trimethylolpropane obtained according to (I)

300 g of the oxethylated trimethylolpropane obtained according to (I) having an oxethylation degree of 3.75 were esterified azeotropically in 50 ml of toluene with 216 g of acrylic acid in the presence of 2.5 g of p-toluene sulphonic acid and 0.2 g of toluhydroquinone, until water could no longer be isolated. At the end of the reaction, the mixture was neutralized with the equivalent quantity of soda, based on p-toluene sulphonic acid, the toluene was distilled off under vacuum (final pressure 1 torr, final temperature of the reaction material 100° C.), and the product was filtered. A light yellow, odourless liquid was obtained having a viscosity of 102 cP (20° C., Höppler viscosimeter), a refractive index $n_D^{20}$ of 1.4738, an OH number of 13 and an acid number of 0.8. The resulting product was used as a reactive diluent for Example 6.

B. Production of the compounds (I) according to the present invention

EXAMPLE 1

1 g of p-toluene sulphonic acid was added to a suspension of 77 g (0.3 mols) of benzil dimethyl ketal in 160 g (~1.8 mols) of cis-2-butene-1,4-diol, and heated to from 50° to 60° C. under a pressure of from 10 to 15 torr. After 45 minutes, a clear solution was obtained, the temperature of which rose to from 65° to 70° C. After a further 45 minutes, the reaction mixture had solidified into a crystal mass. After a total of 4 hours, the material was recrystallized from isopropanol, and 80 g (96%) of 2-benzoyl-2-phenyl-4,7-dihydro-1,3-dioxepin were obtained as colourless crystals having a melting point of from 118° to 119° C.

EXAMPLE 2

A mixture of 21 g (0.1 mol) of benzil, 53.5 g (~0.6 mol) of cis-2-bentene-1,4-diol and 0.5 g of p-toluene sulphonic acid were stirred for 9 hours at from 50° to 60° C. under a pressure of from 10 to 13 torr. The reaction product was dissolved in dichloromethane, washed with water until neutral, the dichloromethane phase was dried over anhydrous sodium sulphate and, after evaporating the filtered solution, 26.7 g of yellow crystals were obtained which, according to NMR analysis, consisted to 70% of 2-benzoyl-2-phenyl-4,7-dihydro-1,3-dioxepin. Fractionated distillation and crystallization of the fraction boiling at from 162° to 168° C./0.4 torr produced 9.9 g of colourless 2-benzoyl-2-phenyl-4,7-dihydro-1,3-dioxepin having a melting point of from 118° to 119° C.

EXAMPLE 3

60.8 g (1.9 mols) of methanol were added with stirring to a suspension of 105 g (0.5 mol) of benzil in 107.1 g (0.9 mol) of thionyl chloride, with cooling to a temperature below 10° C. The mixture was initially stirred until room temperature was reached, and then it was stirred for 2 hours at 50° C. 52.8 g (0.6 mol) of cis-2-butene-1,4-diol were added to the clear, pale yellow solution, and volatile products were distilled off at 10 torr and 50° C. The mixture was then stirred for 3 hours at from 60° to 65° C. under normal pressure, 15 g of potassium carbonate and 200 ml of isopropanol were added, and the reaction product was precipitated by the dropwise addition of 100 ml of water. 110.4 g of 2-benzoyl-2-phenyl-4,7-dihydro-1,3-dioxepin were obtained, having a melting point of from 115° to 119° C. After recrystallizing from isopropanol, the melting point was from 118° to 119° C.

EXAMPLE 4

The solution of 52.8 g (0.6 mols) of cis-2-butene-1,4-diol in 36 g of isopropanol was added dropwise at from 0° to 5° C. to a suspension of 105 g (0.5 mols) of benzil in 119 g (1 mol) of thionyl chloride. The reaction mixture was allowed to warm to room temperature and was then stirred for 3 hours at 50° C. Volatile reaction products were distilled off at 10 torr/50° C. and the reaction mixture was then maintained at a temperature of from 50° to 60° C. for 2 hours. After adding 10 g of potassium carbonate and 200 ml of isopropanol, the reaction product was precipitated by the dropwise addition of 100 ml of water. 95.3 g of ochre-coloured crystals were obtained which had been recrystallized from isopropanol. M.p. 112°–116° C.

C. Production of a compound (II) according to the present invention

EXAMPLE 5

2-Benzoyl-2-phenyl-4,5-dihydro-1,3-dioxepin 500 mg of $H_2Ru[P(C_6H_5)_3]_4$ were added to 15.0 g of 2-benzoyl-2-phenyl-4,7-dihydro-1,3-dioxepin under nitrogen. The reaction mixture was stirred mechanically at 140° C. After two hours another 250 mg of $H_2Ru[P(C_6H_5)_3]_4$ were added, and stirring was continued for a further two hours period. After cooling to 20° C., 200 ml of ether were added. The ethereal layer was washed twice each time with 100 ml of water and dried over potassium carbonate. After filtration, 2.0 g of charcoal were added, and the solution was refluxed for half an hour. After filtration, the solution was evaporated to about 100 ml volume and 50 ml of petrol ether were added. When the solution cooled, 12.9 g of 2-benzoyl-2-phenyl-4,5-dihydro-1,3-dioxepin separated as colourless crystals. M.p. 78°–79° C.

D. Use of the compounds according to the present invention

The parts stated in the following are parts by weight.

EXAMPLE 6

A radiation-hardenable lacquer, consisting of 150 parts of binder 1, 112.5 parts of hexene diol-1,6-bisacrylate, 77.5 parts of reactive diluent according to A 2 II and 8.5 parts of the photo-initiators specified in Table 1 was applied to art paper in an 8 μm thick film by means of a wire-covered metal rod.

The coated samples were then passed under a Hanovia ultra violet light source (80 W/cm, spacing 8 cm) on an adjustable conveyor belt. The speeds which produced scratch-resistant, solvent-fast lacquerings are stated in Table 1.

TABLE 1

| Initiator | Reactivity (m/min) |
| --- | --- |
| Benzil dimethyl ketal | 5 (comparison) |
| 2-benzoyl-2-phenyl-4,7-dihydro-1,3-dioxepin | 5 |
| 2-benzoyl-2-phenyl-1,3-dioxolane | 2.5 (comparison) |
| 2-benzoyl-2-phenyl-5,5-dimethyl-1,3-dioxane | 2.5 (comparison) |

EXAMPLE 7

A radiation-hardenable lacquer, consisting of 100 parts of binder 2 and 2.5 parts of the photo-initiators stated in Table 2 was applied to a glass plate in a 50 μm or 250 μm thick film, and immediately hardened under a UV light source at a belt velocity of 5 m/min. After storing for 2 hours, the pendulum hardnesses were determined according to DIN 53 157.

TABLE 2

| Photo-initiator | Pendulum Hardness (sec) 50 μm | 250 μm | |
| --- | --- | --- | --- |
| Benzil dimethyl ketal | 49 | 38 | (comparison) |
| 2-benzoyl-2-phenyl-4,7-dihydro-1,3-dioxepin | 58 | 50 | |
| 2-benzoyl-2-phenyl-1,3-dioxolane | + | | (comparison) |
| 2-benzoyl-2-phenyl-5,5-dimethyl-1,3-dioxane | | | (comparison) |

+ After 2 passages, lacquer not scratch-resistant and slightly tacky.

In order to test the yellowing, the samples stated in Table 2 were covered on half a side in the case of benzil dimethyl ketal and 2-benzoyl-2-phenyl-4,7-dihydro-1,3-dioxepin and then re-illuminated under a UV light source in 3 passages at 5 m/min. The results of this yellowing test are stated in Table 3.

TABLE 3

| Initiator | |
| --- | --- |
| Benzil dimethyl ketal | Considerable yellowing |
| 2-benzoyl-2-phenyl-4,7-dihydro-1,3-dioxepin | slight yellowing |

EXAMPLE 8

Reactivities of different 2-benzoyl-2-phenyl-1,3-dioxa-alkanes or alkenes

A radiation-hardenable lacquer, consisting of 100 parts of binder 2 and 2.5 parts of the photo-initiators stated in Table 4 was applied to a glass plate in a 50 μm or 250 μm thick film and immediately hardened under a UV light source at a belt velocity of 5 m/min.

TABLE 4

| Initiator | 50 μm | 250 μm |
| --- | --- | --- |
| 2-benzoyl-2-phenyl-1,3-dioxane | tacky | tacky |
| 2-benzoyl-2-phenyl-1,3-dioxepane | not tacky not scratch-resistant | not tacky not scratch-resistant |
| 2-benzoyl-2-phenyl-4,7-dihydro-1,3-dioxepin | not tacky scratch resistant | not tacky scratch resistant |
| 2-benzoyl-2-phenyl-1,3-dioxolane | almost free from tackiness, not scratch-resistant | almost free from tackiness, not scratch-resistant |

We claim:
1. A compound corresponding to the following formula:

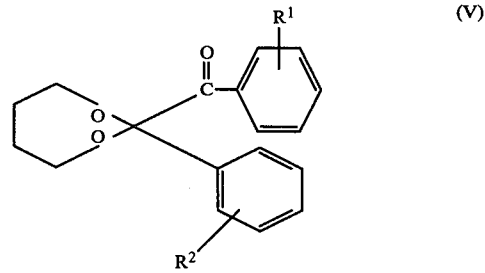

(V)

wherein
$R^1$ and $R^2$ independently represent a hydrogen atom, a $C_1$–$C_4$ alkoxy or alkyl radical, or a halogen atom.

2. A compound according to claim 1, characterised in that the $C_1$–$C_4$ alkyl radical is a methyl radical.

3. A compound according to claim 1 or 2 characterised in that the halogen atom is a chlorine atom.

* * * * *